United States Patent [19]

Verbrugge et al.

[11] 4,008,287

[45] Feb. 15, 1977

[54] PROCESS FOR THE PREPARATION OF CYCLOPROPANE DERIVATIVES

[75] Inventors: Pieter A. Verbrugge; Elisabeth W. Uurbanus, both of Amsterdam, Netherlands

[73] Assignee: Shell Oil Company, Houston, Tex.

[22] Filed: June 17, 1975

[21] Appl. No.: 587,783

Related U.S. Application Data

[63] Continuation-in-part of Ser. No. 359,930, May 14, 1973, abandoned.

[52] U.S. Cl. .................... 200/648 D; 260/649 R; 260/649 F; 260/650 R; 260/650 F; 252/426

[51] Int. Cl.$^2$ ................ C07C 23/04; C07C 23/18; C07C 17/00

[58] Field of Search ....... 260/648 D, 649 R, 650 R, 260/649 F, 650 F

[56] References Cited

UNITED STATES PATENTS

| 3,265,714 | 8/1966 | Robinson | 260/648 D |
| 3,265,744 | 8/1966 | Robinson | 260/648 D |
| 3,359,252 | 12/1967 | Nerdel et al. | 260/648 D |

*Primary Examiner*—D. Horwitz

[57] ABSTRACT gem-dihalocyclopropane derivatives are prepared by reacting olefinic compounds with a dihalocarbene in the presence of an improved catalyst.

6 Claims, No Drawings

PROCESS FOR THE PREPARATION OF CYCLOPROPANE DERIVATIVES

CROSS-REFERENCE TO RELATED APPLICATIONS

This application is a continuation-in-part of Ser. No. 359,930, filed May 14, 1973 now abandoned.

BACKGROUND OF THE INVENTION

There is a strong evidence (see page 36 "Divalent Carbon" by Jack Hine, The Ronald Press Comp., New York, 1964) that upon treatment with an aqueous solution of a strong base a haloform undergoes the following reactions to give the reactive intermediate dihalocarbene (dihalomethylene):

$$CHHal_3 + OH^- \rightleftarrows CHal_3^- + H_2O$$

$$CHal_3^- \rightarrow CHal_2 + Cl^-$$

In the above equations Hal represents a halogen atom. The dihalomethylene readily reacts with water to form carbon monoxide and hydrogen halide.

Makosza et al (see Tetrahedron Letters 53 (1969) 4659 – 62) have contacted aqueous sodium hydroxide with chloroform containing an olefin in the presence of a catalytic amount of triethylbenzylammonium chloride. They found that the corresponding gem-dichlorocyclopropane derivative was formed:

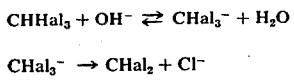

SUMMARY OF THE INVENTION

New and improved catalysts for the reaction of olefinic compounds with dihalocarbenes have now been discovered. The invention accordingly can be generically defined as: in the preparation of gem-dihalocyclopropane derivatives by contacting an aqueous phase containing an alkali metal hydroxide and an organic phase containing both a haloform and an olefinic compound in the presence of a catalyst, the improvement which comprises employing as the catalyst a tri(cyclo)alkyl onium compound having the general formula

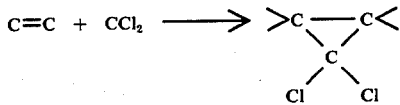

in which $R^1$, $R^2$ and $R^3$ each is alkyl or cycloalkyl of up to 40 carbon atoms, Z is an atom of an element of Group VIA of the Periodic Table of the Elements having an atomic number of more than 15 and Y is a hydroxide or other anion.

High yields of gem-dihalocyclopropane derivatives are often obtained when the onium compounds of formula I are employed as catalysts.

Examples of the onium salts which may be used are iodides, bromides, chlorides, fluorides, alkyl sulfates, tetrafluoroborates and hydrocarbon arylsulfonates, such as tosylates.

Of the tri-(cyclo)alkyl onium compounds of formula I — those of sulfur, selenium and tellurium — those of sulfur exhibit a particularly high activity. $R^1$, $R^2$ and $R^3$ in formula I may be straight-chain or branched-chain alkyl or cycloalkyl, or up to, for example, 40 carbon atoms each, preferably up to 20 carbon atoms each. Trimethyl onium compounds of formula I exhibit a relatively low activity. In contradistinction, (cyclo)alkyl onium compounds of formula I having more than 3 carbon atoms per molecule exhibit a very high activity. The three alkyl groups may be the same, two may be the same and the third different or the three groups may all be different. Examples of very active catalysts are triethylsulfonium iodide, di-sec-decyl-methylsulfonium chloride, n-hexadecyldimethylsulfonium methyl sulfate, sec-dodecyl-sec-hexadecylethylsulfonium ethyl sulfate, sec-hexadecyldimethylsulfonium iodide, sec-hexadecylmethylethylsulfonium tosylate, sec-hexadecyldimethylsulfonium tosylate, trimethylsulfonium bromide, di-n-butylmethylsulfonium iodide. The trialkylsulfonium compounds may easily be prepared by converting an alpha-alkene with hydrogen sulfide into a sec-mercaptan, reacting this sec-mercaptan with another alpha-alkene molecule to form a di-sec-alkyl sulfide and reacting this sulfide with an alkylating agent, for example diethyl sulfate.

The catalysts used in the process according to the present invention may be added to the aqueous and/or organic phase or may be formed in situ. Examples included later herein illustrate in situ preparation. Onium compounds of formula I can be prepared in situ starting from a di(cyclo)alkyl sulfide (selenide, telluride) and a (cyclo)alkyl halide. It has been found that some organic sulfur compounds not falling within the scope of formula I nevertheless exhibit some catalytic activity. It is believed that these compounds are at least partly converted in situ into compounds falling within the scope of formula I. The following examples illustrate this finding. Trialkylsulfoxonium iodides are reduced to trialkylsulfonium iodides, di-n-butylsulfide is alkylated with chloroform to di-n-butyl-dichloromethylsulfonium chloride, dimethyl sulfone is reduced to dimethyl sulfide which is alkylated by chloroform to dimethyldichloromethylsulfonium chloride, and chloroform alkylates phenyl-di-(phenylsulfinylmethyl)-phosphine oxide to the corresponding mono- and disulfonium chlorides.

A physical mixture of any one of the above-mentioned onium compounds may be used as the catalyst. It is possible to use a compound having two or more of the onium structures mentioned in formula I in one molecule.

$R^1$, $R^2$ and $R^3$ may represent substituted hydrocarbyl groups. A hydroxyl group is an example of a substituent.

Ethylenically unsaturated compounds, generally, react with dihalomethylenes generated in situ to form gem-dihalocyclopropane derivatives. This reaction may be represented by means of the following equation:

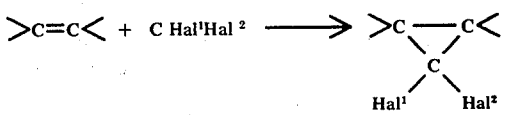

in which Hal[1] and Hal[2] each represent a halogen atom. Hal[1] and Hal[2] may be the same or different. Examples of ethylenically unsaturated compounds which may be used are:

1. straight and branched alkenes with terminal double bonds, such as ethene, propene, 1-butene, 1-pentene, 1-hexene, 1-heptene, 1-octene, 3-methyl-1-butene, 3-methyl-1-hexene, 1-decene and 1-alkenes with more than 10 carbon atoms per molecule.

2. 2-alkenes, 3-alkenes and alkenes in which the double bond is even further removed from a terminal carbon atom, for example 2-pentene, 2-hexene, 3-heptene, 2-methyl-2-butene, 2-octene, 3-nonene and internal alkenes with 10 or more carbon atoms per molecule.

3. di-, tri- and polyalkenes; these alkenes may be conjugated or non-conjugated. For example, butadiene is converted into 2,2,2',2'-tetrachlorobicyclopropyl; other examples of starting compounds are norbornadiene and hexamethyldewarbenzene.

4. cyclic ethylenically unsaturated compounds having a carbon-carbon double bond in the ring; very good results have been obtained with cycloalkenes, particularly with cyclohexene, which is converted into 7,7-dihalonorcarane.

5. substituted ethylenically unsaturated compounds. Examples of substituents are: (a) aromatic groups: phenyl or naphthyl groups, whether or not substituted, such as in styrene (converted into 1,1-dihalo-2-phenylcyclopropane), alphamethylstyrene (converted into 1,1-dihalo-2-phenyl-2-methylcyclopropane), trans-trans-diphenylbutadiene-1,3, , tetraphenylbutadiene (which takes up two dihalomethylene groups), cyclooctatetraene (converted into 9,9-dichloro-bicyclo(6,1,0-nonatriene-(2,4,6)), trans-stilbene (converted into 1,1-dihalo-2,3-diphenylcyclopropane), and cyclododecatriene. (b) halogen atoms: fluorine, chlorine, bromine and iodine atoms; (c) alkoxy groups: butoxyethene (converted into 1,1-dihalo-2-butoxycyclopropane) and 2-propoxypropene (converted into gem-dichloro-2-methyl-2-propoxycyclopropane).

It has been found that alkenecarboxylic acids form an exception to the general rule, in that the base used to generate the dihalocarbene attacks the alpha-hydrogen atom or alkyl moiety (bonded to the carbon atom bearing the carboxyl moiety) to give products other than that desired. To prepare gem-dihalocyclopropanecarboxylic acids from such acids, it is necessary to use an ester or amide thereof, then convert the resulting gem-dihalocyclopropanecarboxylic acid ester or amide to the acid. This procedure for preparing gem-dihalocyclopropanecarboxylic acid esters and amides forms the subject-matter of our application Ser. No 359,931, now Pat. No. 3,917,667 filed on the same date as the parent specification, Ser. No. 359,930.

Also, ethylenically unsaturated compounds having both a carbonitrile group and a (alpha) hydrogen atom bonded to the same double-bonded carbon atom of the ethylene moiety almost do not form gem-dihalocyclopropane derivatives, but form black high molecular weight tar-like products. The corresponding olefins not having an alpha-hydrogen atom, instead having an alkyl or cycloalkyl group bonded to the alpha-carbon atom, readily form the corresponding gem-dihalocyclopropane carboxylic and derivatives.

The haloform which is used has the general formula

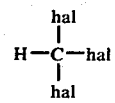

in which each hal represents a halogen atom, viz. a fluorine, chlorine, bromine or iodine atom. The halogen atoms present in the haloform may be the same or different; they may be present in all possible combinations. Examples of haloforms are $CHF_3$, $CHF_2Cl$, $CHFCl_2$, $CHCl_3$, $CHIBr_2$ and $CHClBrI$. Very good results have been obtained with $CHCl_3$.

The aqueous alkali metal hydroxide is preferably a strong aqueous solution with a concentration of preferably at least 30% by weight and in particular of at least 40% by weight alkali metal hydroxide. The maximum concentration of the alkali metal hydroxide in the solution is the concentration of a saturated solution at the temperature at which the process is effected. Solid alkali metal hydroxide may be present. The alkali metal hydroxides which are used, are those of lithium, sodium, potassium, rubidium and cesium. Very good results have been obtained with aqueous sodium hydroxide having a concentration of at least 45% by weight.

Conversion of the olefinic compound to the gem-dihalocyclopropane compounds may be effected by simply mixing: (a) the olefinic compound, (b) a haloform, (c) an aqueous alkali metal hydroxide, and (d) the catalyst; the mixing being conducted for a sufficient time to permit the reaction to go to completion. The mixing should be vigorous, because this improves the yield of, and the selectivity of conversion of the olefinic compound to, the desired gem-dihalocyclopropane derivative. In most cases, conversion will be complete in about one to about five hours time.

Suitably the conversion may be conducted at temperatures within the range of from about 0° C to about 200° C. Ordinarily it will be found to be desirable that the conversion be carried out at a temperature of at least 20° C, but below about 100° C, with mildly elevated temperatures — say from 30°–60° C — being about optimum from the practical conduct of the conversion.

The process is conveniently carried out at atmospheric pressure.

The molar ratio in which the haloform and the olefinic compound and the molar ratio in which the haloform and the alkali metal hydroxide are employed may vary within a wide range and are not critical. The more haloform and the more alkali metal hydroxide are used, relatively, the more rapid the reaction proceeds. Preferably the olefin/haloform molar ratio lies between 1:1 and 1:20, while the preferred haloform/alkali metal hydroxide molar ratio is between 1:1 and 1:10. Molar ratios outside the preferred two ranges are not excluded.

The catalyst is usually employed in an amount which may be indicated by the expression "catalytic amount". The minimum amount of catalyst is that amount which gives the smallest noticeable catalytic effect. The catalyst/haloform molar ratio is preferably between 1:10 and 1:10,000, but molar ratios 1:<10 and 1:>10,000 are not excluded. Excellent results have been obtained with catalyst/haloform molar ratios between 1:100 and 1:1000.

The process may be effected in the presence or in the absence of a solvent. Suitable solvents are: n-alkanes, for example n-pentane, n-hexane and n-heptane; ethers, for example ethers with straight alkyl groups, in particular diethylether, and cyclic ethers, in particular dioxane. The solvents may be used in an amount ranging within wide limits, for example in a haloform/solvent weight ratio in the range between 0.1:1 and 20:1. Weight ratios outside this range are not excluded. Chlorinated hydrocarbons, in particular dihalomethanes, are particularly useful solvents, because they lead to a considerable increase of the yield of gem-dihalocyclopropane derivatives. With dichloromethane yields of 100% or nearly 100% have been obtained.

Since the gem-dihalocyclopropane product is essentially insoluble in the aqueous phase of the final reaction mixture, the product can be recovered by phase separation and recovery from the organic phase by orthodox techniques, such as evaporation of the solvent, followed by recrystallization from a suitable liquid; by extraction of the organic phase with a selective solvent (such as ether) for the product. If, because of the physical character of the final reaction mixture, phase separation does not appear feasible (the final mixture is an apparently intractable emulsion, or the like), the product may be recovered by extraction of the mixture with a suitable selective solvent such as ether.

Conduct of the process of the invention in specific cases is shown in the following examples:

EXAMPLE I

In a flask provided with a one-blade paddle mixer, a mixture of 1.64 grams of cyclohexene, 23.7 grams of chloroform, 20 milliliters of 50%w aqueous sodium hydroxide, 5 milliliters of dichloromethane, 1 milliliter of n-octane (to serve as a GLC marker) and 0.010 gram of the catalyst indicated in Table I was stirred vigorously at 40° C. Samples were taken after stirring had been started at the times indicated in Table I. Table I presents the yields of 7,7-dichloronorcarane. The selectivity to the latter compound was 100% in all cases. A dash indicates that no analysis was effected.

TABLE I

| Catalyst | Yield of 7,7-dichloronorcarane, %, after ... hours | | | |
|---|---|---|---|---|
| Very active catalysts | 0.5 | 1 | 2 | 3 |
| triethylsulfonium iodide | 100 | — | — | — |
| same, at 25° C | 100 | — | — | — |
| methyl-di-sec-decylsulfonium chloride | 60 | — | — | 80 |
| same with 0.025 g. catalyst | 85 | 90 | — | 100 |
| dimethyl-n-hexadecylsulfonium methyl sulfate | 100 | — | — | — |
| sec-dodecyl-sec-hexadecylethyl sulfonium ethyl sulfate | 100 | — | — | — |

TABLE I-continued

| Catalyst | Yield of 7,7-dichloronorcarane, %, after ... hours | | | |
|---|---|---|---|---|
| Very active catalysts | 0.5 | 1 | 2 | 3 |
| sec-hexadecyldimethyl sulfonium iodide | 70 | 72 | 75 | 75 |
| sec-hexadecylmethylethyl-sulfonium tosylate | 60 | 70 | 80 | 90 |
| sec-hexadecyldimethylsulfonium tosylate | 50 | 70 | 75 | 80 |
| trimethylsulfonium bromide | 25 | 80 | 100 | — |
| di-n-butylmethylsulfonium iodide | — | — | — | 90 |
| di-n-butylmethylselenonium iodide | 30 | — | 40 | 44 |
| trimethylsulfoxonium iodide | — | 1 | 2 | 3 |
| trimethylsulfonium iodide | — | 2 | 4 | 7 |
| di-n-butyl sulfide | 2 | 3 | 3.5 | 4 |
| dimethyl sulfone | — | — | — | 2 |
| 1,3,5-trithiacyclohexane | 3 | — | — | — |
| di-n-butyldisulfide and methyl iodide | — | — | 7 | — |

The di-n-butylmethylsulfonium iodide was prepared in situ starting from di-n-butylsulfide and methyl iodide. Di-n-butylmethylselenonium iodide was prepared in situ starting from di-n-butylselenide and methyl iodide.

EXAMPLE II

Three experiments were carried out, each with another catalyst and in the way as described in Example I, with this difference: that 20 grams of bromoform instead of 23.7 grams of chloroform was used. Table II presents the yields of 7,7-dibromonorcarane at the times indicated. The selectivity to the latter compound was 100% in all cases. A dash indicates that no analysis was effected.

TABLE II

| Catalyst | Yield of 7,7-dibromonorcarane, %, after ... hours | | | |
|---|---|---|---|---|
| | 0.5 | 1 | 2 | 3 |
| sec-dodecyl-sec-hexadecylethylsulfonium ethyl sulfate | 10 | 30 | 35 | 40 |
| triethylsulfonium iodide | 50 | — | — | 70 |

EXAMPLE III

Two experiments were carried out in the manner described in Example I. The catalysts used, the quantities applied, the products formed and the yields of these products are listed in Table III. The temperature was 35° C, except as otherwise stated.

TABLE III

| Starting material | | catalyst | chloroform grams | diethylether, grams | 50% w NaOH ml. | product formed | yield of product, % |
|---|---|---|---|---|---|---|---|
| grams | compound | | | | | | |
| 6.8 | 3-methyl-2-butenylacetate | 0.020 g. sec-dodecyl-sec-hexadecylethyl-sulfonium ethyl sulfate | 20 | 20 | 20 | 2,2-dichloro-3,3-dimethylcyclopropylmethyl acetate | 80% |
| 18 | methyl 3-methyl-2-butenyl ether | 0.030 g. same | 100 | 0 | 60 | methyl 2,2-dichloro-3,3-dimethylcyclopropylmethyl ether | 52% after 5 hours in this case at 40° C |

The process provided by this invention is particularly of interest for preparing fungicidally and insecticidally active gem-dihalocyclopropane derivatives of the formula

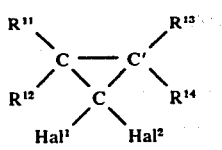

wherein $Hal^1$ and $Hal^2$ each is halogen atom; $R^{11}$ is hydrogen or alkyl or phenyl group; $R^{12}$ and $R^{13}$ each is hydrogen or alkyl group; and $R^{14}$ is carbonitrile (when $R^{13}$ is alkyl). These fungicidally active compounds are especially active against fungal diseases of rice crops, in particular against rice blast (pyricularia oryzae). These compounds and their utility are described in German Patent 2,219,710).

What is claimed is:

1. In a process for preparing gem-dihalocyclopropane derivatives by reacting an alkene optionally substituted by one or more aromatic groups or halogen atoms with a dihalocarbene in the presence of a catalyst, the improvement which comprises employing as catalyst an onium compound having the general formula $$\left[ \begin{array}{c} R^1 \\ | \\ Z-R^3 \\ | \\ R^2 \end{array} \right]^+ \left[ Y \right]^- \quad (I)$$

in which $R^1$, $R^2$ and $R^3$ each is alkyl or cycloalkyl of up to 40 carbon atoms, Z is an atom of an element of Group VIA of the Periodic Table of the Elements having an atomic number of more than 15 and Y is an anion.

2. The improvement according to claim 1, in which the onium compound has more than 3 carbon atoms per molecule.

3. The improvement according to claim 2 wherein the reaction is conducted in the presence of a chlorinated hydrocarbon as a solvent.

4. The improvement according to claim 3 in which the solvent is dichloromethane.

5. The improvement according to claim 1 wherein the onium catalyst is sec-dodecyl-sec-hexadecylethylsulfonium ethyl sulfate.

6. The improvement according to claim 1 wherein the onium catalyst is di-n-butylmethylselenonium iodide.

* * * * *

UNITED STATES PATENT AND TRADEMARK OFFICE
CERTIFICATE OF CORRECTION

PATENT NO. : 4,008,287
DATED : February 15, 1977
INVENTOR(S) : PIETER A. VERBRUGGE and ELISABETH W. UURBANUS It is certified that error appears in the above-identified patent and that said Letters Patent are hereby corrected as shown below:

Cover sheet (Page 1)

After section [63], insert

--[30] Foreign Application Priority Data

May 16, 1972 Great Britain .... 22911/72 --.

Signed and Sealed this

Seventeenth Day of May 1977

[SEAL]

Attest:

RUTH C. MASON
Attesting Officer

C. MARSHALL DANN
Commissioner of Patents and Trademarks